United States Patent [19]
Abramovici et al.

[11] 4,057,617
[45] Nov. 8, 1977

[54] METHOD OF LABELING PROTEINS WITH TECHNETIUM

[76] Inventors: Jean Abramovici, 127, Av. du Pesage; André Marie Ermans, 2, Av. de la Foret, both of Ixelles, 1050 Brussels; Omer Jeghers, 95A, rue Fechereux, 4561 Neufchateau, all of Belgium

[21] Appl. No.: 635,774

[22] Filed: Nov. 26, 1975

[30] Foreign Application Priority Data

May 15, 1975 Belgium ................................ 829128
Aug. 12, 1975 Belgium ................................ 159144

[51] Int. Cl.² ................ A61K 37/04; A61K 33/00; A61K 43/00
[52] U.S. Cl. ....................... 424/1; 250/303; 252/301.1 R; 424/1.5; 424/9
[58] Field of Search ................ 424/1, 1.5, 9; 252/301.1 R; 250/303

[56] References Cited
U.S. PATENT DOCUMENTS

| 3,725,295 | 4/1973 | Eckelman et al. | 424/1 |
| 3,740,418 | 6/1973 | Rajamani et al. | 424/1 |
| 3,784,453 | 1/1974 | Dworkin et al. | 424/1 |
| 3,787,565 | 1/1974 | Nouel et al. | 424/1 |
| 3,863,004 | 1/1975 | Wolfangel | 424/1 |
| 3,872,226 | 3/1975 | Haney et al. | 424/1 |
| 3,933,996 | 1/1976 | Charlton et al. | 424/1 |

OTHER PUBLICATIONS

Wong, D. W. et al., J. Nucl. Med., vol. 16, No. 5, pp. 343-347 (1975).
Harwig, J. F. et al., International J. Appl. Radiation and Isotopes, vol. 27, pp. 5-13 (1976).
Steigman, J. et al., Int. J. Appl. Rad. Isot., vol. 26, pp. 601-609 (1975).
Gwyther, M. et al., Int. J. Appl. Rad. Isot., vol. 17, pp. 485-486 (1966).
Lin, M. et al., J. Nucl. Med., vol. 12, No. 5, pp. 204-211 (1971).
Caro, R. A. et al., Int. J. Appl. Rad. Isot. vol. 26, pp. 527-532 (1975).

Primary Examiner—Benjamin R. Padgett
Assistant Examiner—T. S. Gron
Attorney, Agent, or Firm—Cushman, Darby & Cushman

[57] ABSTRACT

Fibrinogen is labeled with $^{99m}$Technetium by reducing pertechnetate at a pH of about 11–12 using a solution of stannous chloride in the presence of a base, then contacting the reduced pertechnetate with fibrinogen. Unwanted lower molecular weight impurities are removed; the labeled product suitably adjusted to a pH of 7–8 to form an injectable isotopic tracer solution.

18 Claims, 4 Drawing Figures

FIG_4.
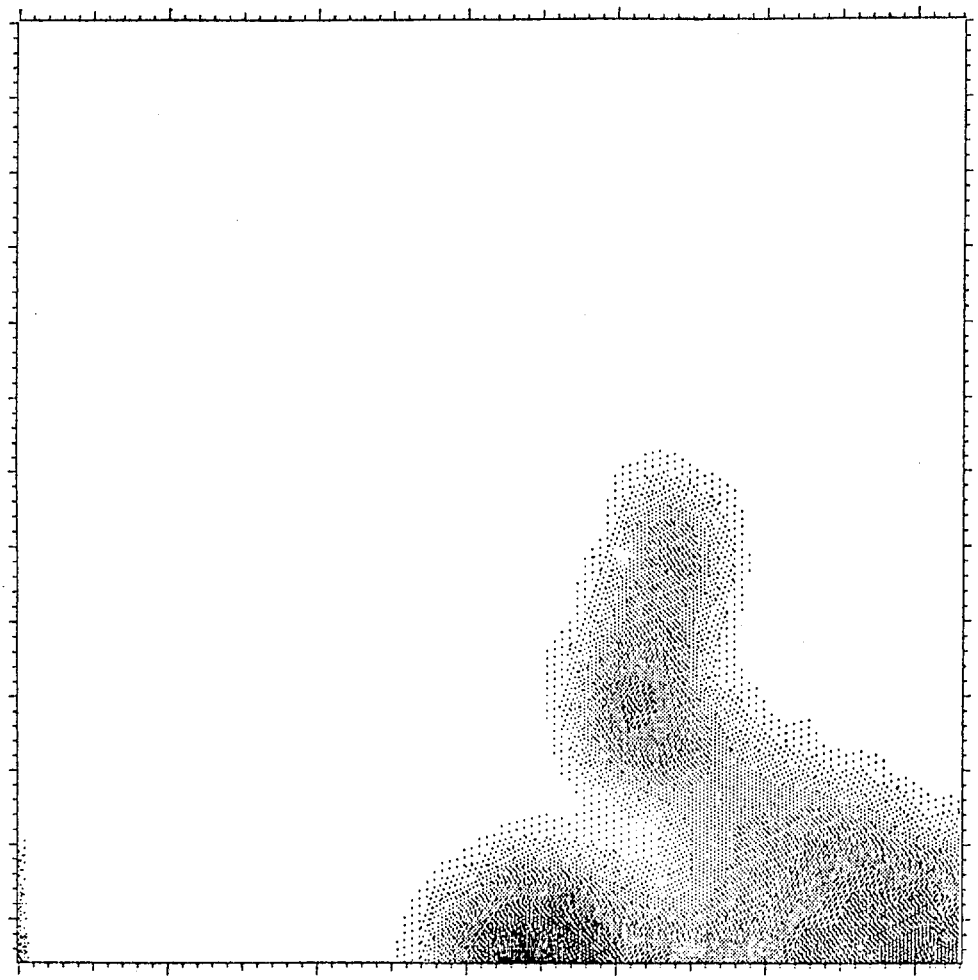

METHOD OF LABELING PROTEINS WITH TECHNETIUM

The invention relates to a method of labeling proteins with $99^m$ technetium, wherein pertechnetate is reduced and the reduced pertechnetate is contacted with at least one protein from the group comprising fibrinogen and immunoglobulins.

Various methods of labeling fibrinogen have been published in the literature. The information relates inter alia to the labeling of fibrinogen with iodine $I^{131}$ or $I^{125}$.

The aforementioned labeling methods comprise the electrolytic method, the enzymatic method, the chloramine-T method and the iodine monochloride method. These methods have a number of disadvantages, due firstly to the use of radioisotopes having a half-life which is excessively long or unsuitable for labeling proteins, and, secondly, to the fact that the energy is not compatible with existing commercial display means, the amount of irradiation is excessive, or the background noise is too great and prevents the detection of thromboses in the pelvic region.

These are the main reasons why it is preferable at present to use methods of labeling with $99^m$ technetium, which has the following important advantages: It is easy to obtain, it has a short half-life, it emits pure gamma radiation having an energy suitable for display by conventional devices and the degree of irradiation is at a minimum.

Most conventional labeling methods, however, are mainly electrolytic. Although the literature mentions labeling with $99^m$ technetium by chemical processes or in the presence of reducing agents such as stannous chloride or ironascorbic acid, it is clear that the results have never been very satisfactory, since the aforementioned agents usually lower the solubility of the reduced pertechnetate, which may adversely affect the labeling of the protein. With regard to the methods of labeling with $99^m$ technetium in which the pertechnetate is reduced electrolytically, they are free, according to the literature, from the aforementioned disadvantages of the known chemical methods and often result in fairly selective labeling of the protein, but the equipment required is complicated and expensive, since zirconium electrodes are normally used for electrolysis.

The invention has yielded the quite unexpected finding that, under certain conditions, chemical methods of labeling proteins with $99^m$ technetium in the presence of reducing agents may be extremely advantageous compared with known labeling methods, more particularly with electrolytic methods, both with regard to the selectivity of labeling and to the yield and stability thereof.

An object of the invention is to provide an economic method of obtaining an injectable solution of a protein from the aforementioned group of substances, labeled with $99^m$ technetium, the method being adapted to take full advantage of the very advantageous properties of technetium as an isotopic tracer and the resulting labeling being more effective and more stable and the technetium being more efficiently bound to the protein than in known methods of labeling.

To this end, according to the invention, the pertechnetate is reduced in the presence of a reducing agent to a pH between 11 and 12 and the mixture containing the protein labeled with technetium obtained by bringing reduced technetium into contact with the protein in question is purified so as to eliminate any degradation products of the protein and any non-bound technetium.

Advantageously the purification consists of separating substances having a molecular weight below 100,000 from the protein.

In a particularly advantageous embodiment, the pertechnetate is reduced at a pH of the order of 11.6.

In a preferred embodiment, pertechnetate in physiological serum is reduced by adding a solution of acetic acid and stannous chloride as reducing agent and subsquently adding a base to bring the pH to the desired value.

The invention also relates to an injectable solution containing at least one protein chosen from the group comprising fibrinogen and immunoglobulins labeled with $99^m$ technetium obtained by the aforementioned method.

Other details and features of the invention will be clear from the following non-limitative description of some advantageous embodiments of the method according to the invention.

FIG. 4 shows an enlarged image from an electrostatic printer showing radioactivity regions corresponding to the fixation of $99^m$ technetium-fibrinogen on regions affected by rheumatoid arthritis in a rat's tail and paw, 19 days after injecting the same dose of Freund's adjuvant as used to obtain the image represented in FIG. 3, and 500 $\mu$ Ci of $99^m$ Tc — fibrinogen.

Figure 1:
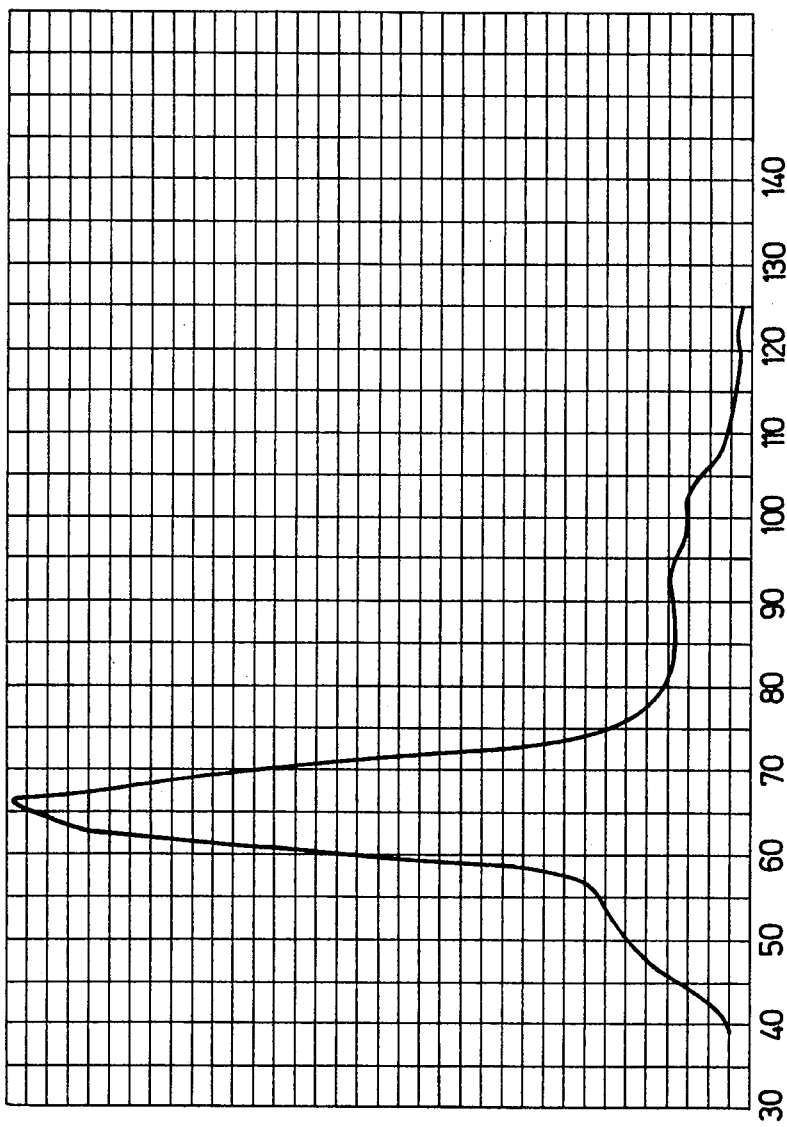
FIG. 1 is a graph obtained by chromatography, the abscissae showing the different fractions of a solution containing fibrinogen labeled with $99^m$ technetium and the ordinate showing the radioactivity of the fraction.
Figure 2:
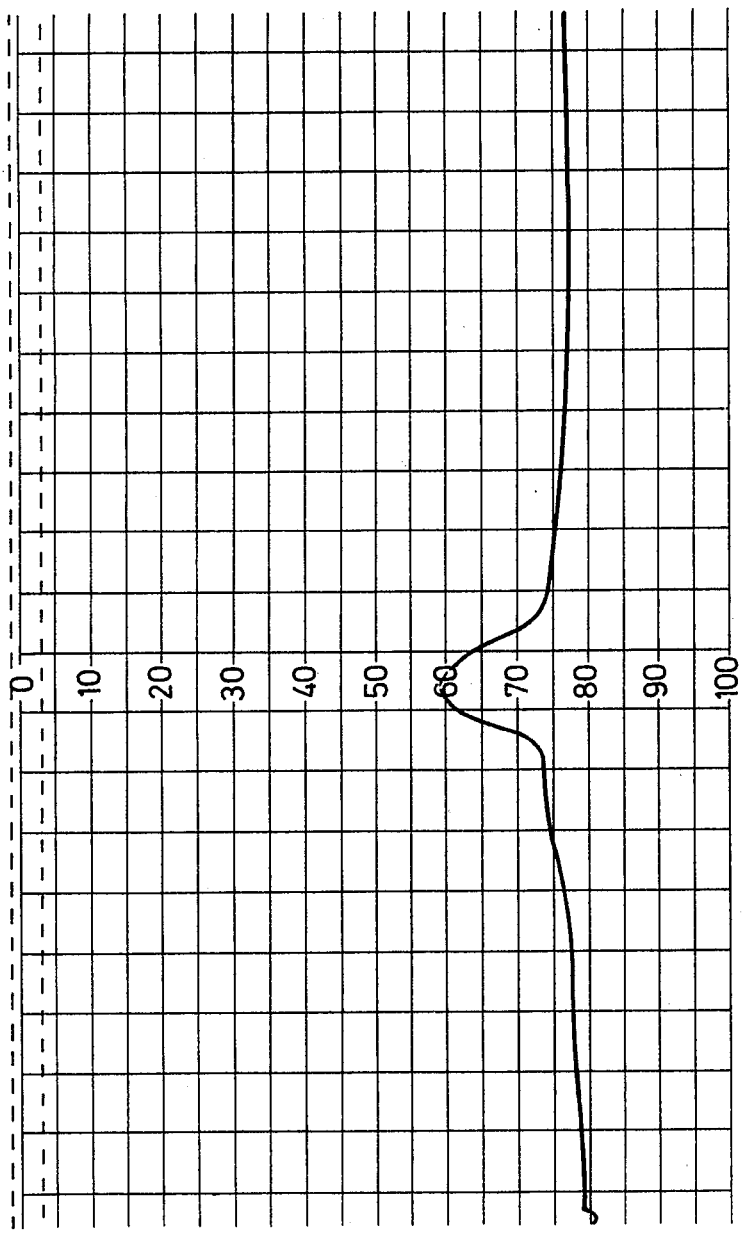
FIG. 2 shows a graph obtained by chromatography, the abscissae showing the different fractions obtained from a solution containing fibrinogen labeled with $99^m$ technetium and the ordinate showing the optical density of the fractions.

The method according to the invention relates to the preparation of an injectable solution of fibrinogen or immunoglobulins labeled with $99^m$ technetium, used as an isotopic tracer.

This radioisotopic complex is particularly useful for specific early radiodiagnosis of inflammatory diseases of the connective tissue such as rheumatoid arthritis, vascular thromboses and malign tumours, more particularly in the liver and brain.

It is advantageous to use lyophilized fibrinogen of human origin which can be injected into man and up to approx. 90% of which is coagulable. The fibrogen is also sterile and is free from Australian antigens and pyrogens. It is preserved in lyophilized form in the presence of sodium salts.

The isotopic tracer used is preferably sterile, apyrogenic $99^m$ Tc pertechnetate ($NaTcO_4$).

Before being put into contact with the protein to be labeled (fibrinogen in the present case) the pertechnetate is reduced, since it is generally accepted that $99^m$Tc obtained in the form of $99^m$ Tc $O_4^-$ must be reduced to the + 4 or + 5 stage before being bound to a molecule.

The choice of pH is very important in this connection. According to the invention, the pH used is of the order of 11 to 12, preferably 11.6.

It is absolutely indispensable to maintain the pH within this range, since, outside this range, it has unexpectedly been found that there is a substantial loss in the efficiency with which the reduced technetium is bound to the protein.

The reducing agent used is preferably stannous chloride, in which case the reduced technetium, when brought into contact with the fibrinogen, becomes bound to the tyrosyl groups of the fibrinogen molecule.

The lyophilized fibrinogen is dissolved in sterile, apyrogenic water and subsequently dialyzed to separate the aforementioned sodium salts.

In a subsequent step, the reduced pertechnetate is vigorously put into contact, e.g. by agitation, with the fibrinogen in solution so as to label it.

The resulting mixture comprising the fibrinogen in solution and the reduced pertechnetate is subsequently brought to a pH between 7 and 8, preferably by adding an aqueous solution of sodium citrate and citric acid. A pH of the order of 7.4 is excellent.

Alternatively, lyophilized fibrinogen can be labeled without the aforementioned dialysis. The subsequent procedure is as before, the mixture comprising the fibrinogen in solution and the reduced pertechnetate being brought to a pH between 7 and 8, preferably 7.4, as before by adding an aqueous solution of sodium citrate and citric acid. To this end, according to the invention, note that the reduction of the pertechnetate, the contacting of the reduced pertechnetate with the fibrinogen in solution and the lowering of the pH of the mixture to between 7 and 8 are preferably done in a nitrogen atmosphere. The nitrogen takes the place of atmosphere oxygen and prevents any oxidation or re-oxidation of the substances present, inter alia the reduced pertechnetate.

According to the invention, the resulting mixture containing technetium-labeled protein is purified to eliminate any degradation products of the protein and any technetium which has not been bound thereto.

Preferably, the purification consists of separating the labeled protein from substances having a molecular weight less than 100,000 or, if required less than 300,000, by conveying the mixture through a suitable membrane which retains substances having a higher molecular weight than those given.

For example, in order to retain substances having a molecular weight greater than 100,000, it is advantageous to use a model 12 Amicon cell comprising a type XM 100 A membrane.

Advantageously, free technetium and technetium bound to molecules having a molecular weight less than 100,000 are eliminated in a first purification step, and all molecules having a molecular weight less than 300,000 are eliminated in a second step.

In some cases, e.g. when lyophilized fibrinogen is labeled without dialysis, it is necessary, before purification proper, to separate colloidal and/or precipitated particles, e.g. precipitated tin particles, which appear during the lowering of the pH of the mixture containing dissolved fibrinogen and reduced pertechnetate. For example, the particules can be retained by a Millipore filter having a pore diameter of 0.22mµ.

Various methods of checking (e.g. column chromatography and immunoelectrophoresis) have shown that the method of purification ensures that most of the degradation products and of the free technetium is eliminated. In the final method it has been found, according to the invention, that about 90% of the $99^m$ technetium is bound, in a very reproducible manner, to the fibrinogen molecule, whereas in some special cases the subsequent two purification operations can yield a technetium-labeled fibrinogen solution in which the amount of technetium bound to a fibrinogen molecule is at least 98%.

In this connection, it may be noted that the previously-mentioned known labeling methods cannot give such a high yield; the yields obtained are approx. 55 to 70%.

The aforementioned two graphs show the efficiency of the method of purification according to the invention and that the labeled product is fibrinogen and is labeled in a very selective manner.

The method according to the invention is further illustrated by the following two examples:

EXAMPLE 1

Reduction of pertechnetate 10 m Ci of pertechnetate in 2 ml physiological serum were reduced by adding firstly, 1 ml of an aqueous solution of 100 ml containing 20 microliter of 96% acetic acid and 10 mg $SnCl_2.2H_2O$, and, secondly, 0.3 ml of 0.1 N NaOH to bring the pH to 11.6.

Processing of the fibrinogen 1 g of lyophilized fibrinogen was dissolved in 100 ml sterile, apyrogenic water. The dissolved fibrinogen was dialyzed at 4° C in Visking 1-8/32 inch dialysis bags against a 0.6% NaCl solution for 18 hours.

The dissolved fibrinogen was divided into 2 ml aliquot parts and preserved in bottles at −20° C.

Labeling proper 2 ml of fibrinogen was agitated at ambient temperature for 15 minutes with the solution containing the reduced technetium. The pH of the resulting mixture was lowered to 7.4 by adding the necessary quantity of a buffer solution containing 10 ml of 0.1 M sodium citrate and 0.5 ml of 0.1 M citric acid.

Purification of the fibrinogen

Any non-bound technetium and any degradation products were eliminated by passing through a model 12 Amicon cell comprising a XM 100 A type membrane.

Final check of the labeled fibrinogen solution

Before being injected, the finally- obtained product was tested for sterility and the absence of pyrogens.

EXAMPLE 2

Reduction of pertechnetate

The procedure was the same as in Example 1, working in a nitrogen atmosphere.

Processing of the fibrinogen 1 g of lyophilized fibrinogen was dissolved in the presence of sodium salts in 100 ml sterile, apyrogenic water. The dissolved fibrinogen was divided into 2 ml aliquot parts which were preserved in bottles at −20° C.

Labeling proper 2 ml of fibrinogen was agitated under nitrogen at ambient temperature for 15 minutes with the solution containing the reduced technetium. The pH of the resulting mixture was reduced from an initial value of 9.6 to 7.4 by adding the required quantity of a solution containing 10 ml of 0.1 M sodium citrate and 0.5 ml of 0.1 M citric acid, in a nitrogen atmosphere as before.

Separation of colloidal and/or precipitated particles appearing during the lowering of the pH Any colloids and precipitated tin are separated by conveying the mixture through a 0.22 m$\mu$ Millipore filter.

Actual purification of the fibrinogen

Same as in Example 1.

Final check of the solution of labeled fibrinogen

As before, the final product is tested before being injected, so as to check that it is sterile and free from pyrogens.

Similarly, the method according to the invention can be used to label immunoglobulins (IgG, IgA, IgM) with technetium.

As already mentioned, fibrinogen and immunoglobulins are labeled for the purpose of early, specific diagnosis of a certain number of diseases such as rheumatoid arthritis, vascular thromboses and malign tumours, more particularly in the liver and brain. The method can show up lesions in the organs by displaying them by means of a scintillation gamma camera.

The following is a comparative study showing the advantages of the method according to the invention ($99^m$ Tc-fibrinogen) compared with the method using $99^m$ Tc $O_4^-$, a tracer substance conventionally used in diagnosing inflammatory diseases of the joints and in rheumatoid arthritis with Freund's adjuvant in the rat.

As is known, the histological picture of rheumatoid arthritis is characterised by an early deposit of fibrin on to the synovial membrane, around which cellular elements accumulate and lead to pannus formation.

At various stages of the development of arthritis after injecting the adjuvant, an identical quantity of one of the two tracers was injected into two groups of rats.

The purpose of the research is shown in the following Table:

TABLE

1. Batches of 3 rats + Freund's adjuvant

500$\mu$ Ci Tc 99mO$_4^-$
   |   |   |   |   |   |   |   |
   |---|---|---|---|---|---|---|
   | 0 | 3 | 6 | 9 | 12 | 15 | 17 | 21 | days
   500$\mu$ Ci Fi Tc 99m 2. Continuous recording of the radioactivity for 30 or 60 minutes.
3. Choice of the regions of interest.
4. Calculation of the activity ratios :
   a. whole paw/whole body
   b. active region/whole paw
   c. active region/inactive region
5. Comparison between these ratios after 5 and 30 minutes.
6. "t by pairing" statistical method.

Figure 3:
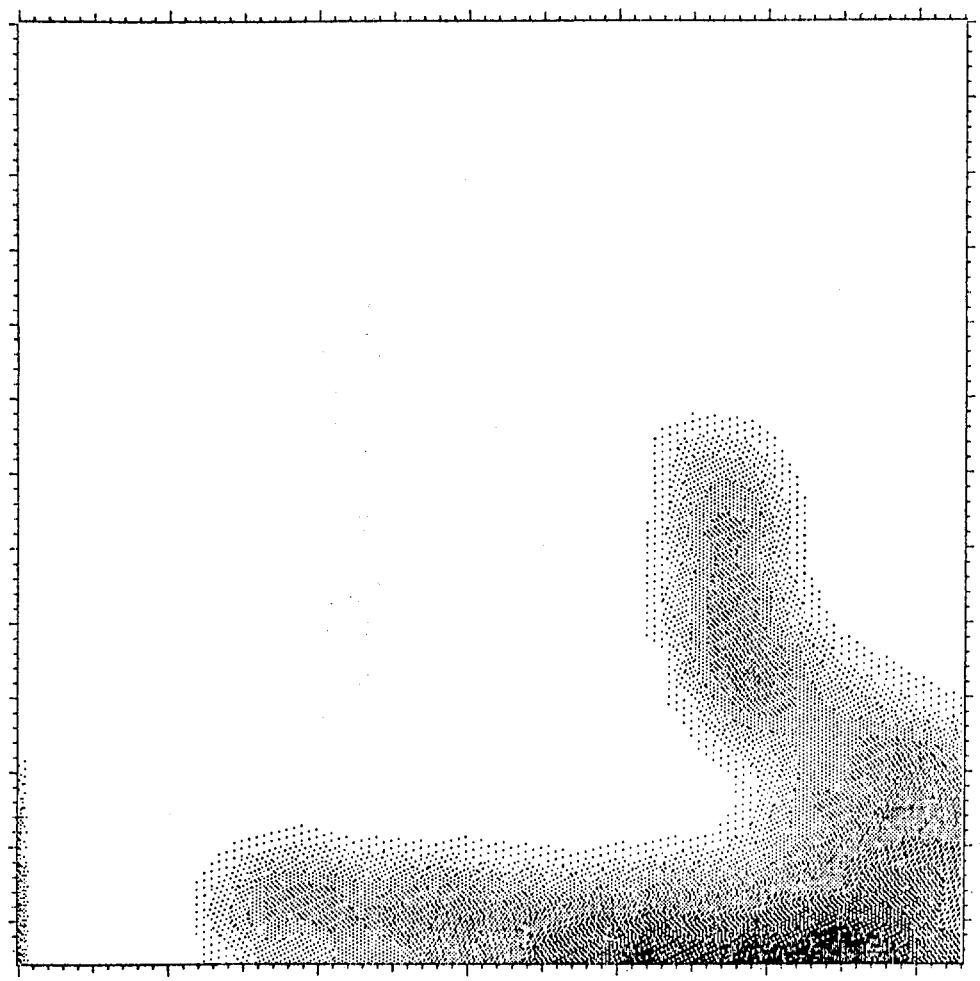
FIG. 3 is an enlarged image from an electrostatic printer showing the radioactivity regions corresponding to the fixation of $99^m$ technetium-pertechnetate on regions affected with rheumatoid arthritis in a rat's tail and paw, 19 days after the injection of Freund's adjuvant and 500 $\mu$ Ci of $99^m$ Tc $O_4^-$.

An analysis of the results, as shown more particularly in FIGS. 3 and 4 of the accompanying drawings, leads to the following conclusions:

a. The distribution of $99^m$ TcO$_4^-$ and $99^m$ Tc-fibrinogen in the diseased joints is quite different; it is uniform for $99^m$ TcO$_4^-$, as can be seen from FIG. 3, which shows a single region of hyperfixation of $99^m$ technetium in the rat's paw and tail, whereas it is heterogeneous for $99^m$ Tc-fibrinogen as can be seen in FIG. 4, which shows two quite distinct hyperfixation regions in the paw and an intense fixation region in the tail.

This difference is due mainly to the different behaviour of the two tracers.

The accumulation of $99^m$ TcO$_4^-$ in a diseased joint is the combined result of two mechanisms:

In a first phase, the accumulation is proportional to the degree of inflammation (intra-vascular phase).

In a second phase, the tracer, after being bound to blood proteins, diffuses into the surrounding tissues (extra-vascular phase).

Tc $99^m-$ fibrinogen does not diffuse into the surrounding tissue.

The degree of fixation is proportional to the amount of fibrin deposited in the affected synovial membrane.

b. A comparison between the diseased region non-diseased region ratio after 5, 30 or 60 minutes shows that the ratio decreases with time in the case of $99^m$ Tc O$_4^-$ but increases in the case of $99^m$ Tc-fibrinogen.

The "t by pairing" statistical analysis is highly significant:

| $\Delta R^*$ at + 5 minutes and 30 minutes | |
|---|---|
| $99^m$ Tc O$_4$ | $99^m$ Tc-fibrinogen |
| $p < 0,001$ | $0,1 \; p < 0,05$ | c. The accumulation of $99^m$ Tc O$_4$, therefore, is the result of a process of vaso-dilatation during a non-specific inflammation, whereas $99^m$ Tc-fibrinogen is bound in a specific manner, associated with the presence of a fibrin deposit on the synovial membrane.

d. $99^m$ Tc-fibrinogen can be used as an isotopic tracer for early, specific diagnosis of rheumatoid arthritis.

e. $99^m$ Tc-fibrinogen can also provide an objective estimate of the progress of the disease.

Of course, the invention is not limited to the embodiments described and may be modified in many ways without departing from the present patent.

We claim:

1. A method of labeling fibrinogen with 99m technetium comprising reducing pertechnetate at a pH of about 11 to 12 by the addition of a solution of acetic acid and stannous chloride in the presence of a base, contacting the thus reduced pertechnetate with fibrinogen thereby labeling the fibrinogen with 99m technetium and purifying the resulting mixture by removing unwanted degradation products of the fibrinogen and non-bound technetium.

2. A method according to claim 1 wherein the pertechnetate is reduced at a pH of the order of about 11.6.

3. A method according to claim 1 wherein the purification includes separating the labeled fibrinogen from substances having a molecular weight less than 100,000.

4. A method according to claim 1 wherein the purification includes separating from the mixture substances having a molecular weight less than 300,000.

5. A method according to claim 1 wherein the purification includes first separating free technetium and technetium bound to molecules having a molecular weight less than 100,000, and in a subsequent step separating molecules having a molecular weight less than 300,000.

6. A method according to claim 3 wherein the mixture is conveyed over a suitable membrane through which substances to be separated from the mixture pass.

7. A method according to claim 1 wherein the pertechnetate is contained in physiological medium.

8. A method according to claim 1 wherein an injectable fibrinogen of human origin is used.

9. A method according to claim 1 wherein lyophilized fibrinogen with buffer salts is used including dissolving the fibrinogen in water to yield a fibrinogen solution, mixing the fibrinogen solution with the reduced pertechnetate for about 15 minutes at ambient temperature, and reducing the pH of the mixture of fibrinogen and reduced pertechnetate to a final pH of 7 to 8.

10. A method according to claim 9 wherein the fibrinogen solution is dialysed to eliminate the buffer salts prior to mixing with the reduced pertechnetate.

11. A method according to claim 9 wherein the final mixture is adjusted to a pH of the order of about 7.4.

12. A method according to claim 9 wherein the pH of the mixture is reduced to the desired value by adding an aqueous solution of sodium citrate and citric acid to produce an injectable solution.

13. A method according to claim 9 wherein prior to the purification step any colloidal substances, precipitated substances or both occurring during the lowering of the pH of the mixture are separated.

14. A method according to claim 13 wherein the mixture is passed through a filter which retains thereon substances to be separated and removed from the mixture.

15. A method according to claim 10 wherein the fibrinogen is labeled in a nitrogen atmosphere.

16. A method of binding 99m technetium to fibrinogen to produce fibrinogen labeled with 99m technetium comprising the steps of:
 1. reducing pertechnetate at a pH of about 11 to 12 by the addition thereto of a solution of acetic acid and stannous chloride in the presence of a base;
 2. contacting the thus reduced pertechnetate with fibrinogen thereby labeling the fibrinogen with 99m technetium;
 3. removing unbound technetium and technetium bound to molecules having a molecular weight less than 100,000, and in a second purification step;
 4. removing all molecules having a molecular weight less than 300,000, thereby producing a product having about 90% or more of the 99m technetium bound to the fibrinogen.

17. A method according to claim 16 wherein at least about 98% of the technetium is bound to the fibrinogen.

18. A method of producing an injectable solution of 99m technetium labeled fibrinogen comprising the steps of:
 1. reducing pertechnetate at a pH of about 11-12 by adding a solution of acetic acid and stannous chloride in the presence of a base;
 2. dissolving lyophilized fibrinogen including buffer salts associated therewith in water yielding a fibrinogen solution;
 3. mixing the fibrinogen solution of step (2) with the reduced pertechnetate of step (1) at ambient temperature for about 15 minutes;
 4. lowering the pH of the solution of step (3) to a final pH of about 7-8 by the addition of an aqueous solution of sodium citrate and citric acid; and
 5. removing fibrinogen degradation products and non-bound technetium, thereby producing an injectable solution of fibrinogen labeled with 99m technetium.

* * * * *